(12) United States Patent
Boinnard

(10) Patent No.: US 11,730,628 B2
(45) Date of Patent: *Aug. 22, 2023

(54) MULTI-THICKNESS GOGGLE LENSES

(71) Applicant: 100% SPEEDLAB, LLC, San Diego, CA (US)

(72) Inventor: Ludovic Francis Boinnard, San Diego, CA (US)

(73) Assignee: 100% SPEEDLAB, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/752,604

(22) Filed: May 24, 2022

(65) Prior Publication Data

US 2022/0280344 A1     Sep. 8, 2022

Related U.S. Application Data

(63) Continuation of application No. 15/236,274, filed on Aug. 12, 2016, now Pat. No. 11,337,860.

(51) Int. Cl.
*A61F 9/02* (2006.01)

(52) U.S. Cl.
CPC .............. *A61F 9/029* (2013.01); *A61F 9/02* (2013.01); *A61F 9/022* (2013.01); *A61F 9/025* (2013.01); *A61F 9/027* (2013.01); *A61F 2250/0036* (2013.01)

(58) Field of Classification Search
CPC .. A61F 9/02; A61F 9/022; A61F 9/025; A61F 9/027; A61F 9/029; G02C 1/04; G02C 1/08; G02C 1/10; G02C 3/00; G02C 7/022; G02C 7/06; G02C 7/08

USPC ............................................ 2/12, 13, 15, 426
See application file for complete search history.

(56) References Cited

U.S. PATENT DOCUMENTS

| | | | | | |
|---|---|---|---|---|---|
| 1,785,929 | A | * | 12/1930 | Bouchard | G02C 1/10 351/83 |
| 2,384,867 | A | * | 9/1945 | Williams | G02C 1/023 351/104 |
| 4,427,271 | A | * | 1/1984 | Fogg | G02C 5/00 351/178 |
| 5,189,447 | A | * | 2/1993 | Oleson | G02C 5/146 2/448 |
| 5,371,554 | A | * | 12/1994 | Aspesi | G02C 11/02 351/52 |

(Continued)

FOREIGN PATENT DOCUMENTS

| | | | |
|---|---|---|---|
| EP | 0038093 A1 | * | 10/1981 |
| EP | 0312465 A1 | * | 4/1989 |

(Continued)

*Primary Examiner* — F Griffin Hall
(74) *Attorney, Agent, or Firm* — Kolitch Romano Dascenzo Gates LLC

(57) ABSTRACT

A multi-thickness lens for a goggle may be disclosed in accordance with various embodiments. The multi-thickness lens may include a portion of a first thickness and a portion of a second thickness. In particular, the multi-thickness lens may be inserted into a goggle, including goggles configured to receive standard lenses. Further, the goggle may include features that may allow the multi-thickness lens to distribute forces and/or stresses to the goggle and/or may include features and/or components adapting the goggle to receive a multi-thickness lens.

16 Claims, 15 Drawing Sheets

(56) References Cited

U.S. PATENT DOCUMENTS

| | | | | |
|---|---|---|---|---|
| 5,455,639 A * | 10/1995 | Magdelaine | G02C 11/12 | 351/44 |
| 5,523,805 A * | 6/1996 | Kuipers | G02C 1/02 | 351/86 |
| 5,526,068 A * | 6/1996 | Markovitz | G02C 7/12 | 351/44 |
| 5,862,529 A * | 1/1999 | Moodie | A61F 9/029 | 2/431 |
| 6,074,059 A * | 6/2000 | Glass | G02C 1/06 | 351/86 |
| 6,718,561 B2 * | 4/2004 | Dondero | A61F 9/025 | 2/436 |
| 7,114,807 B2 * | 10/2006 | Tagawa | G02C 11/08 | 351/158 |
| 7,281,793 B2 * | 10/2007 | D'Agostino | B24D 5/02 | 351/158 |
| 7,290,294 B2 * | 11/2007 | Kita | A61F 9/025 | 2/443 |
| 8,096,653 B2 * | 1/2012 | Matsui | B29D 11/00634 | 351/158 |
| 8,636,360 B2 * | 1/2014 | Wiand | G02C 7/02 | 351/178 |
| 8,641,188 B2 * | 2/2014 | DiChiara | G02C 1/04 | 351/86 |
| 8,992,009 B2 * | 3/2015 | Austin | G02C 5/22 | 351/111 |
| 9,086,581 B2 * | 7/2015 | Zider | G02C 5/00 | |
| 10,012,846 B1 * | 7/2018 | Santinelli | G02C 1/10 | |
| 10,254,561 B1 * | 4/2019 | Santinelli | G02C 1/10 | |
| 2004/0226080 A1 * | 11/2004 | Shiue | A63B 33/004 | 2/426 |
| 2005/0206841 A1 * | 9/2005 | Saderholm | G02C 11/08 | 351/159.08 |
| 2005/0280908 A1 * | 12/2005 | Tanaka | G02B 7/026 | 359/811 |
| 2009/0201463 A1 * | 8/2009 | Carlson | G02C 1/04 | 351/159.67 |
| 2013/0314660 A1 * | 11/2013 | Chen | G02C 1/08 | 351/86 |
| 2016/0202496 A1 * | 7/2016 | Billetz | G02C 1/10 | 351/86 |
| 2017/0357103 A1 * | 12/2017 | Jiang | G02C 1/06 | |
| 2018/0188555 A1 * | 7/2018 | Quere | G02B 27/0172 | |

FOREIGN PATENT DOCUMENTS

| | | | | |
|---|---|---|---|---|
| WO | WO-8705123 A1 * | 8/1987 | | |
| WO | WO-2016124866 A1 * | 8/2016 | | G02C 1/08 |
| WO | WO-2018123195 A1 * | 7/2018 | | G02C 1/10 |

\* cited by examiner

MULTI-THICKNESS GOGGLE LENSES

TECHNICAL FIELD

One or more embodiments relate generally to goggles and, more particularly, to sport goggles.

BACKGROUND

Sport goggles are worn by users for various sports or activities, such as motorsports, powersports, snowsports, watersports, biking, or the like, to protect users' eyes. A sport goggle typically includes a goggle frame which is compatible with a specific type of lens or accessories.

SUMMARY

Goggle systems and methods are provided in accordance with one or more embodiments that may include a multi-thickness lens. In accordance with an embodiment, a goggle lens may be disclosed. The goggle lens may include a goggle lens perimeter portion including one or more attachment features configured to couple to a goggle frame, wherein at least a portion of the goggle lens perimeter portion is a first thickness and a goggle lens viewing portion coupled to the goggle lens perimeter portion. The goggle lens viewing portion may be a second thickness different from the first thickness.

BRIEF DESCRIPTION OF THE DRAWINGS

Embodiments of the invention and their advantages are best understood by referring to the detailed description that follows. It should be appreciated that like reference numerals are used to identify like elements illustrated in one or more of the Figures.

DETAILED DESCRIPTION

A multi-thickness lens for sports goggles is disclosed in accordance with various embodiments. The multi-thickness lens may include one or more portions at a first thickness and one or more portions at a second thickness. Additionally, the multi-thickness lens may include additional portions at certain thicknesses. In certain embodiments, the multi-thickness lens may be adapted to be retrofitted onto an existing goggle. In certain such embodiments, the lens may include features to allow for the lens to fit onto lens mounting features of the existing goggle.

Sports goggles may provide protection to the user of the goggles. For examples, sports goggles may protect the user from dust, stones, foliage, mechanical parts, and other debris that may strike the user. For example, a goggle may be compatible with lenses of a first thickness. Accordingly, the goggle may include slots or other interfaces that are configured to receive lenses of the first thickness. Such goggle may not be compatible with lenses of a second thickness as the second thickness may be too thick or too thin to be inserted into the slots or other interfaces. Thus, if the user and/or manufacturer required a lens of a different thickness, a new sport goggle must be used.

The multi-thickness lens may be thicker in certain portions to prevent damage from debris that strikes the lens from striking the user and/or prevent damage to the lens itself while including features to allow the multi-thickness lens to be compatible with goggle configured to receive lenses of other thicknesses. Additionally, the multi-thickness lens may include features to distribute such stresses experienced by the lens to further prevent damage. Such features may include features on the lens itself or features of the goggles.

Figure 1:
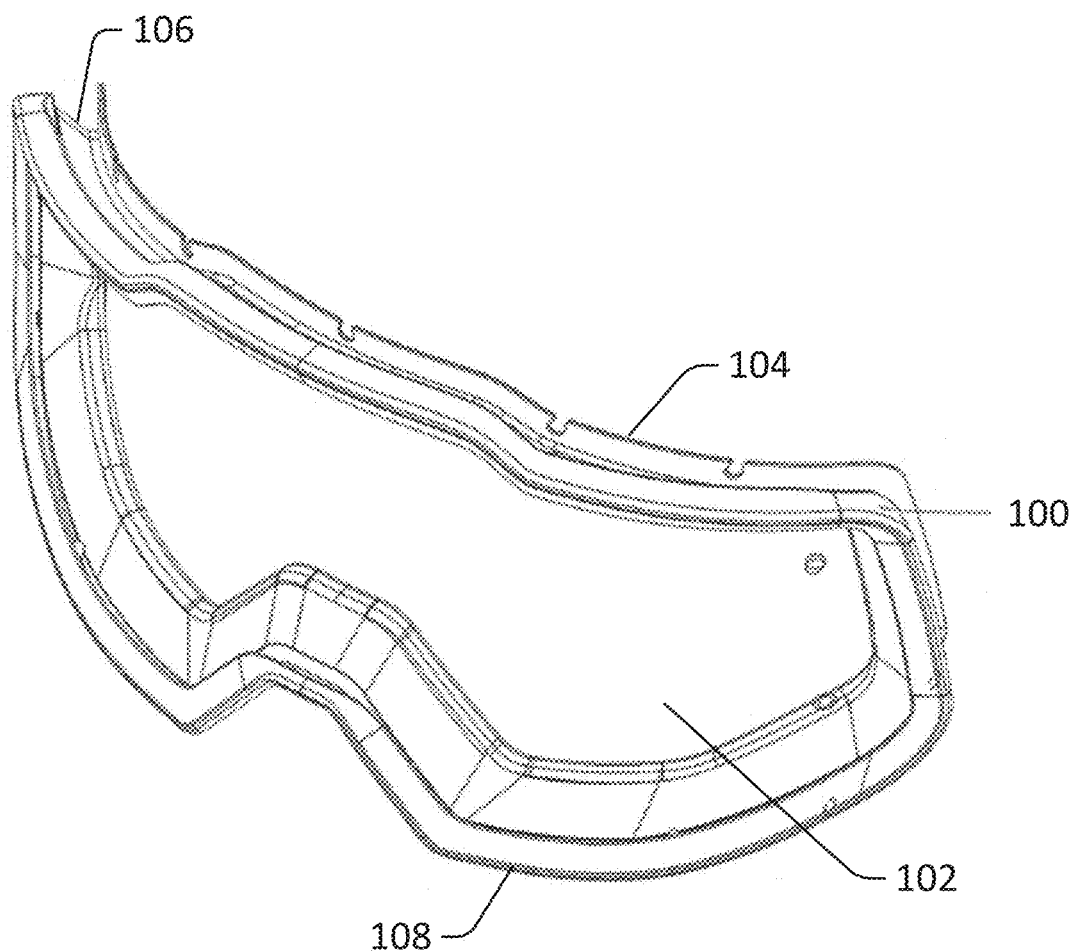
FIG. 1 illustrates an isometric view of a sports goggle, in accordance with an example of the disclosure.
Figure 2:
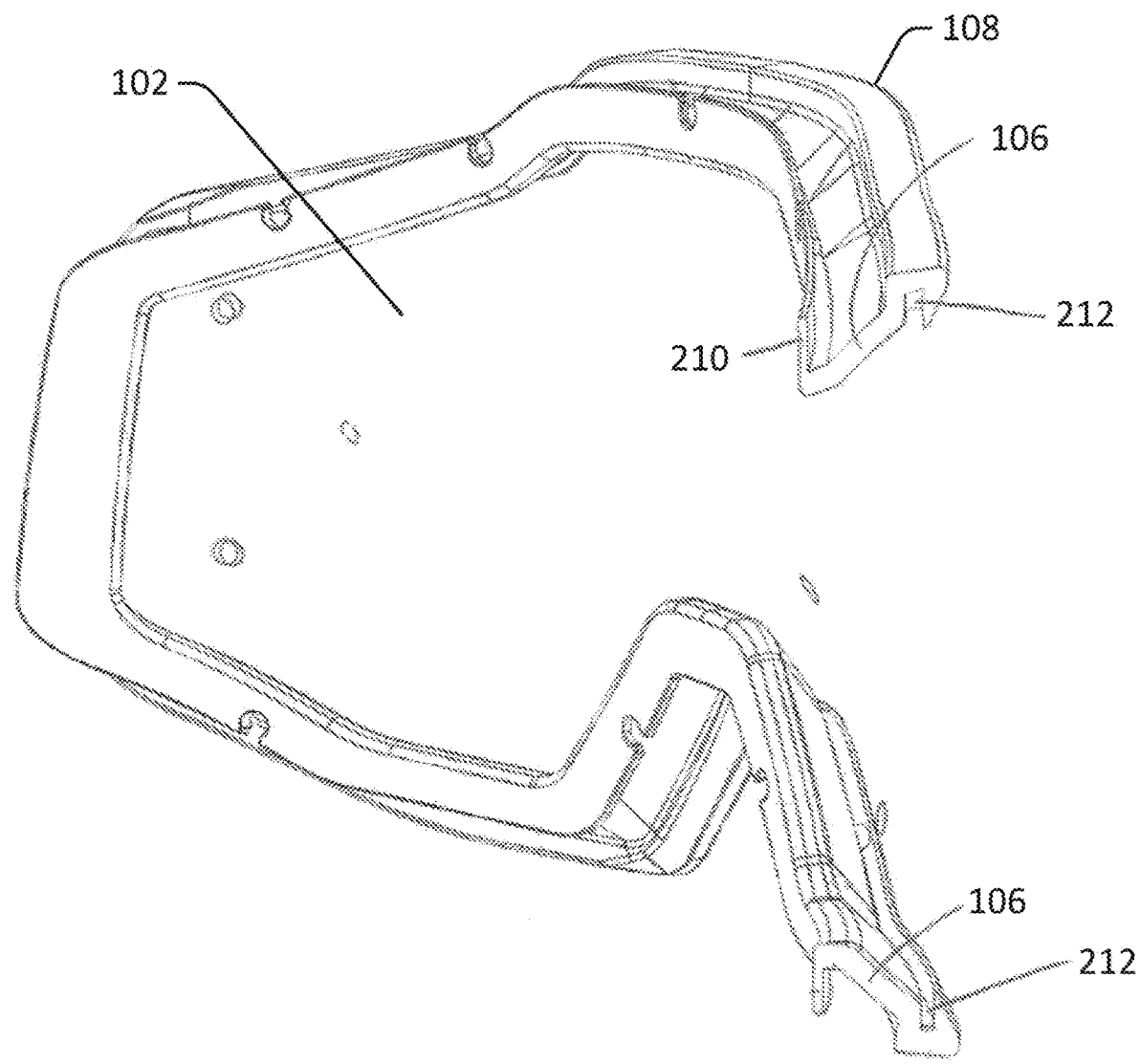
FIG. 2 illustrates a cutaway view of a sports goggle, in accordance with an example of the disclosure.

FIG. 1 illustrates an isometric view of a sports goggle, in accordance with an example of the disclosure. As shown in FIGS. 1 and 2, goggle 100 may include a lens 102, a gasket 104, and a first goggle frame portion 106, and a second goggle frame portion 108. The lens 102 may be received by a lens receiving portion of the goggle 100 and may be disposed substantially at a front end of goggle 100. In certain embodiments, the first goggle frame portion 106 and the second goggle frame portion 108 may fully or partially "sandwich" the lens 102 between them when assembled, thus holding the lens 102 in place. In certain such embodiments, the first goggle frame portion 106 may be disposed on a rear end (e.g., the portion closer to the face of the user) of the goggle 100 and the second goggle frame portion 108 may be disposed on a front end (e.g., the portion farther from the face of the user) of the goggle 100. In certain embodiments, the first goggle frame portion 106, the second goggle frame portion 108, and/or other portions of the goggle 108 may be made from one or multiple materials. Such materials may be rigid or flexible and may include plastics, composites, wood, metal, cardboard, rubber, silicone, and/or other such materials.

The lens 102 may be replaceable. As such, in certain embodiments, the goggle 100 may be configured such that the lens 102 may be replaced from the goggle 100 and replaced with another lens. In certain embodiments, the lens 102 may then be held in place with adhesives, mechanical fasteners, through friction and/or other features preventing substantial movement of the lens 102, and/or through other techniques.

The gasket 104 may be configured to contact a user's face. In certain embodiments, the gasket 104 may seal or aid in sealing the interior of the goggle 100 from moisture, dust, rocks, UV rays, and/or other environmental objects. As such, the gasket 104 may be made from a flexible material such as rubber or silicone. In certain embodiments, the gasket 104 may include vent holes to allow for ventilation.

Goggle 100 may have a loop shape with particular contours that may accommodate the eyes and nose of a user. In particular, goggle 100 may include a right field vision region, a left field vision region, and a nose region. The right field vision region may be configured to surround a right eye of a user, the left field vision region may be configured to surround a left eye of the user, and the nose region may be configured to rest on the nose of the user. In particular, the nose region of the goggle 100 may have a dome shape to accommodate the nose of the user.

The first goggle portion 106 and/or the second goggle portion 108 may be formed continuously around the loop shape of the goggle 100. As such, the first goggle portion 106 and/or the second goggle portion 108 may have similar contours at the right field vision region, the nose region, and the left field vision region of the goggle 100, respectively. In certain embodiments, different portions of the goggle 100 may gradually change from facing in the rear direction to facing in the downward direction at, for example, the dome shaped nose region of the goggle 100 and thus, the gasket 104, the first goggle portion 106, and/or the second goggle portion 108 may be configured to have a continuous and seamless contact with the face of the user around the user's eyes and around the user's nose. The gasket 104, the first goggle portion 106, and/or the second goggle portion 108 may have cutouts that may provide additional flexibility around the nose region to provide additional comfort to the user.

The first goggle portion 106, and/or the second goggle portion 108 may include slit openings at the right end and the left end. The slit openings may be configured to accommodate a goggle strap that may be used to wrap around a user's head to fasten the goggle 100 to the user. For example, two ends of the goggle strap may be threaded through the two slit openings, respectively. The first goggle portion 106, and/or the second goggle portion 108 also may include recesses at the right and left ends near the slit openings. The recesses may be configured to accommodate the goggle strap when the goggle strap wrap around the left and right sides of the goggle 100.

FIG. 2 illustrates a cutaway view of a sports goggle, in accordance with an example of the disclosure. FIG. 2 may illustrate an embodiment of the goggle 100 where the first goggle portion 106 and the second goggle portion 108 are interconnected and may, thus, be produced as one part. In such an embodiment, the first goggle portion 106, the second goggle portion 108, and/or a combination of the first goggle portion 106 and the second goggle portion 108 may form a groove 212. The groove 212 may extend through a portion or all around that of the goggle 100. The groove 212 may be configured to receive the lens 102. In certain embodiments, features forming the groove 212 may be flexible and/or may be configured to be disassembled. In such embodiments, the lens 102 may be removed from the goggle 100 and a new lens may be fitted.

In certain embodiments, a part of the first goggle portion 106 may form a part of the groove 212 and a part of the second goggle portion 108 may form another part of the groove 212. In such embodiments, the first goggle portion 106 may be coupled to the second goggle portion 108 to form the groove 212. When the first goggle portion 106 is coupled to the second goggle portion 108, the lens 102 may be secured within the groove 212. The first goggle portion 106 may also be configured to be decoupled from the second goggle portion 108. When decoupled, the lens 102 may be removed from the groove 212.

In other embodiments, portions of the goggle 100 (e.g., the first goggle portion 106 and/or the second goggle portion 108) and/or the lens 102 may be flexible. In such embodiments, the lens 102 may be removed by flexing the portions of the goggle 100 and/or flexing the lens 102. In certain such embodiments, the lens 102 may be removed through a combination of disassembly of the goggle 100 and flexing of certain portions of the goggle 100 and/or the lens 102.

FIGS. 3A-F illustrate orthogonal views of a multi-thickness lens, in accordance with an example of the disclosure. FIGS. 4A-C illustrate isometric views of a multi-thickness lens, in accordance with an example of the disclosure. FIGS. 3A-F and 4A-C illustrate a lens 102 that includes a goggle lens perimeter portion 320 and a goggle lens viewing portion 322. The lens 102 may also include attachment features 324A-I.

In certain embodiments, the goggle lens viewing portion 322 and the goggle lens perimeter portion 320 may be different thicknesses. In certain such embodiments, the goggle lens viewing portion 322 may be a first thickness and the goggle lens perimeter portion 320 may be a second thickness. In certain other such embodiments, the goggle lens viewing portion 322 and/or the goggle lens perimeter 320 may be varying thicknesses (e.g., the thickness may change from one part of the goggle lens viewing portion 322 and/or the goggle lens perimeter 320 to another part such that the goggle lens viewing portion may be a first thickness range and the goggle lens perimeter portion 320 may be a second thickness range).

The goggle lens perimeter portion 320 may be configured to be coupled to the goggle 100. In certain embodiments, the goggle lens perimeter portion 320 may be configured to be inserted within the groove 212. The goggle lens perimeter portion 320 may be configured (e.g., sized or dimensioned) to be inserted within the groove 212 and/or coupled to the goggle 100. The goggle lens viewing portion 322 may be thicker than the goggle lens perimeter portion 320 to provide additional protection to the user. In such embodiments, the goggle lens perimeter portion 320 may be a second thickness or vary within a second thickness range to fit within the groove 212 while the goggle lens viewing portion 322 may be a first thickness or vary within a first thickness range. In certain embodiments, the goggle lens viewing portion 322, or a portion thereof, may be thicker than the goggle lens perimeter portion 320. Certain such embodiments may, for example, have the goggle lens perimeter portion 320 be between 0.2 to 1.6 millimeters thick (e.g., 0.8 millimeters thick) and the goggle lens viewing portion 322 be between 1.2 to 3.2 millimeters thick (e.g., 1.6 millimeters thick).

In certain embodiments, the goggle lens viewing portion 322 may be, at least, a first material while the goggle lens perimeter portion 320 may be, at least, a second material. For example, the first material may be a material less susceptible to damage. The second material may be a material that may aid in the insertion of the lens 102 into the groove 212 to couple the lens 102 to the goggle 100. Examples of such materials may include plastics, glass, plexiglass, and/or other appropriate materials. In certain embodiments, such materials or a portion of such materials may be coated (e.g., with anti-fog coating or anti-ultraviolet radiation coating) and/or may be polarized. For embodiments where the goggle lens viewing portion 322 and the goggle lens perimeter portion 320 are the same material or different materials, the goggle lens viewing portion 322 and the goggle lens perimeter 320 may be formed separately (e.g., the portions may be produced separately and coupled together) or together (e.g., produced at the same time) via, for example, injection molding, blow molding, 3D printing, machining, and/or other production processes. In embodiments where the goggle lens viewing portion 322 and the goggle lens perimeter portion 320 are formed separately, the portions may then be coupled together through bonding, gluing, mechanical fastening, welding, ultrasonic welding, and/or other processes after the portions are formed.

In certain embodiments, the goggle lens viewing portion 322 may be configured such that the differences in thickness do not affect the vision of the user. As such, the transitions between thicknesses may be positioned away from the likely field of view of the user. Additionally, certain embodiments may include one or more smooth transition between the different thicknesses while other embodiments may include one or more stepped transitions between the different thicknesses. Certain other embodiments of the multi-thickness lens 102 may include three or more portions of different thicknesses, or may include smooth transitions between portions of different thicknesses.

Additionally, in certain embodiments, a portion of the lens 102 may be configured to contact the goggle 100 when the lens 102 is coupled to the goggle 100. In such embodiments, the lens 102 and/or the goggle 100 may include features that may help distribute forces and/or stresses experienced by the lens 102 to the goggle 100. In certain such embodiments, the thicker goggle lens viewing portion 322 may bear higher stresses than the thinner goggle lens perimeter portion 320. As such, configuring the lens 102 to distribute forces and/or stresses and/or to the goggle 100 may allow the goggle lens viewing portion 322 of the lens 102 to receive higher stresses (e.g., from a rock strike) while not damaging the goggle lens perimeter portion 320.

In certain such embodiments, the lens 102 may include, for example, a lip and/or another feature that may be configured to contact a portion of the goggle 100 (e.g., the first goggle frame portion 106 and/or the second goggle frame portion 108). Such contact may form a load path that may distribute stresses received by the goggle lens viewing portion 322 through to the portion of the goggle 100. In certain such embodiments, for example, the transition between the goggle lens perimeter portion 320 and the goggle lens viewing portion 322 may form a lip. The lip may be configured to contact a portion of the goggle 100 (e.g., a portion of the first goggle frame portion 106 and/or the second goggle frame portion 108) and thus form the load path. Additionally, certain embodiments may include additional features on the lens 102 and/or the goggle 100 (e.g., gaskets, mechanical features such as hooks and/or snaps, fasteners, adhesives, and/or other features) that may allow for forces to be transferred from the lens 102 to the first goggle frame portion 106 and/or the second goggle frame portion 108.

The lens 102 may couple to the goggle 100 via, for example, one or more attachment features 324A-I. The attachment features may, for example, be one or more holes, slots, cutouts, pins, hooks, snaps, and/or other features that may receive a corresponding feature on the first goggle frame portion 106 and/or the second goggle frame portion 108 (e.g., a hole on the lens 102 may be configured to be inserted within a pin on the first goggle frame portion 106 and/or the second goggle frame portion 108). Such attachment features 324A-I may be disposed on the top, sides, and/or bottom of the lens 102. In certain embodiments, the lens 102 may include, for example, five slots on the top of the lens 102, two slots on the bottom of the lens 102, and 2 slots near a nose portion of the lens 102. In certain such embodiments, the attachment features 324A-I may be disposed regularly or semi-regularly along a perimeter of the lens 102.

Figure 3A:
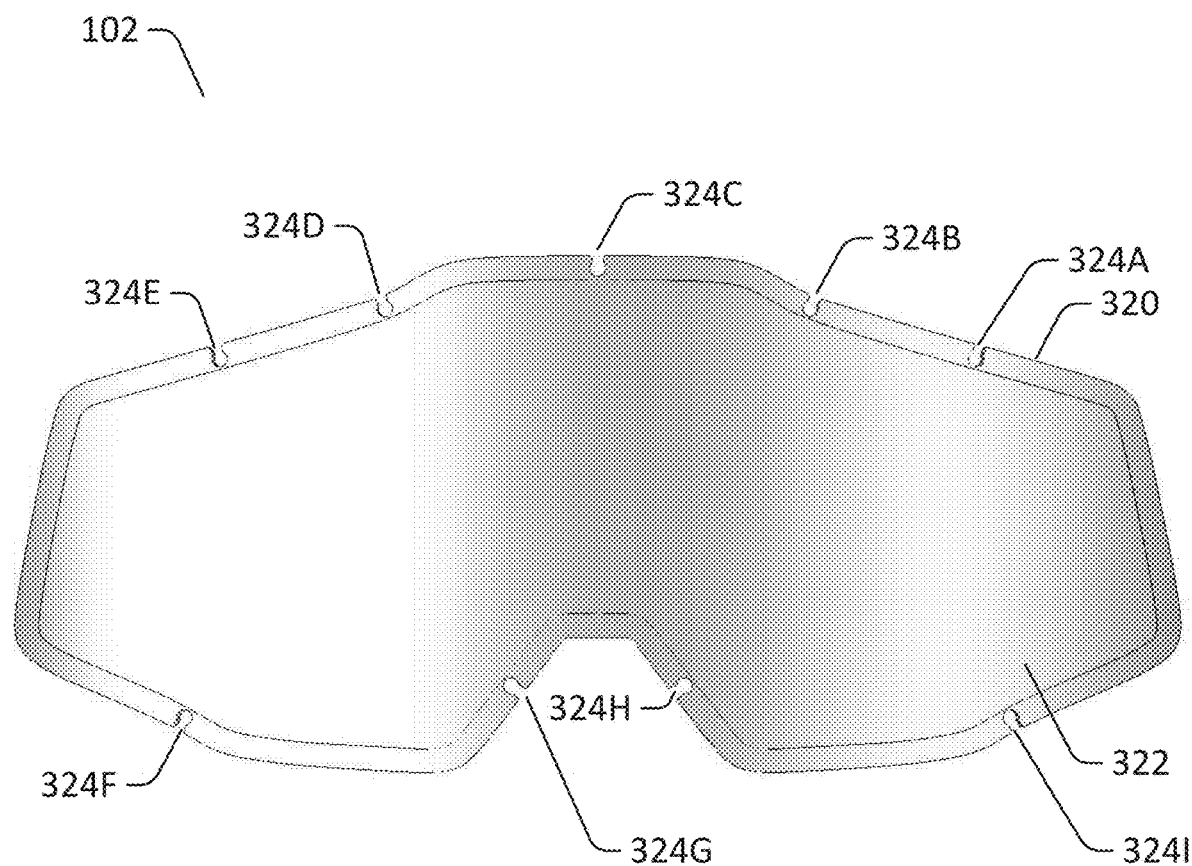
FIGS. 3A-F illustrate orthogonal views of a multi-thickness lens, in accordance with an example of the disclosure.
Figure 3B:
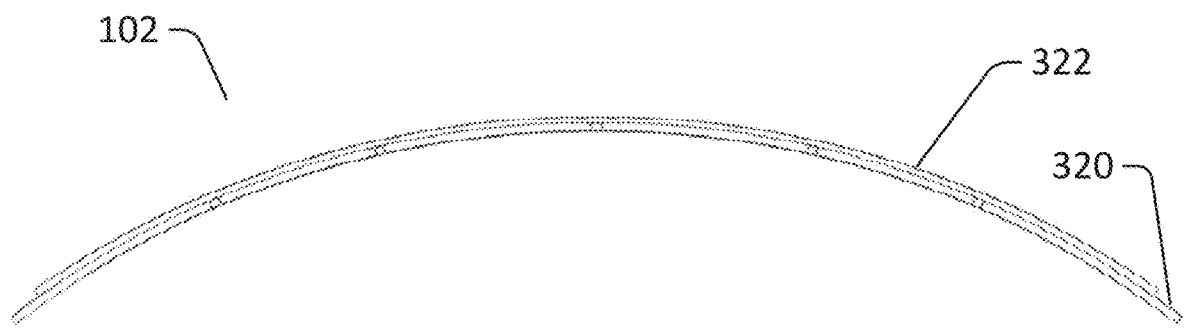
Figure 3C:
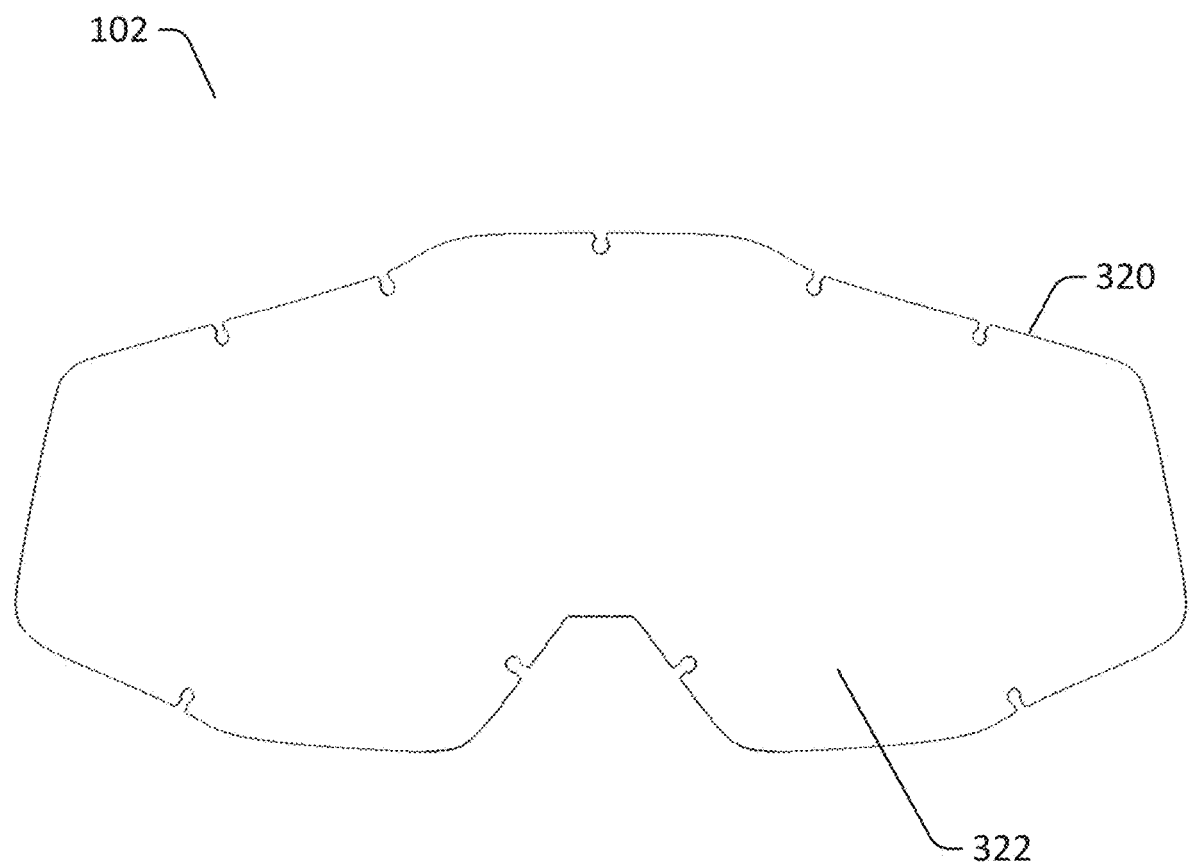
Figure 3D:
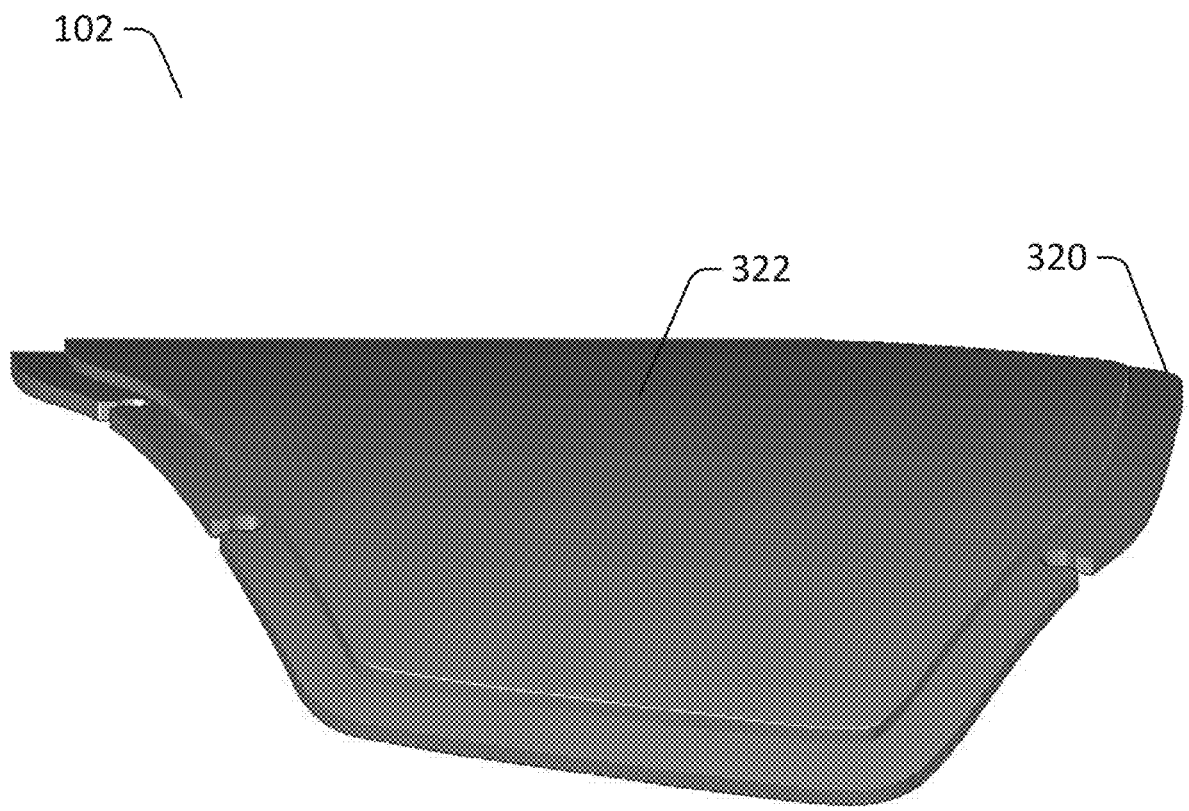
Figure 3E:
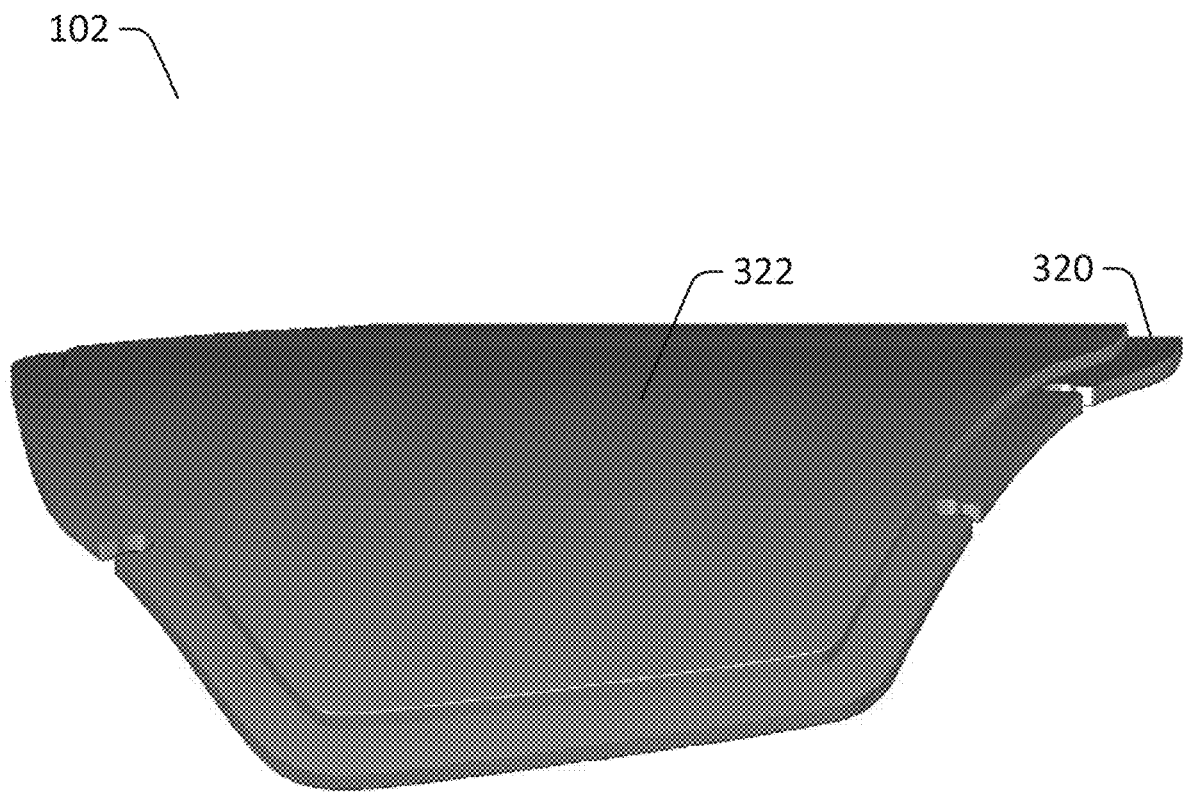
Figure 3F:
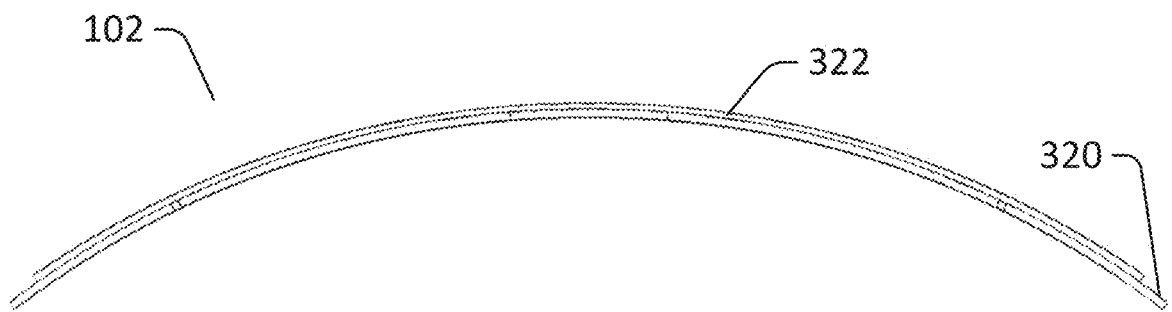
Figure 4A:
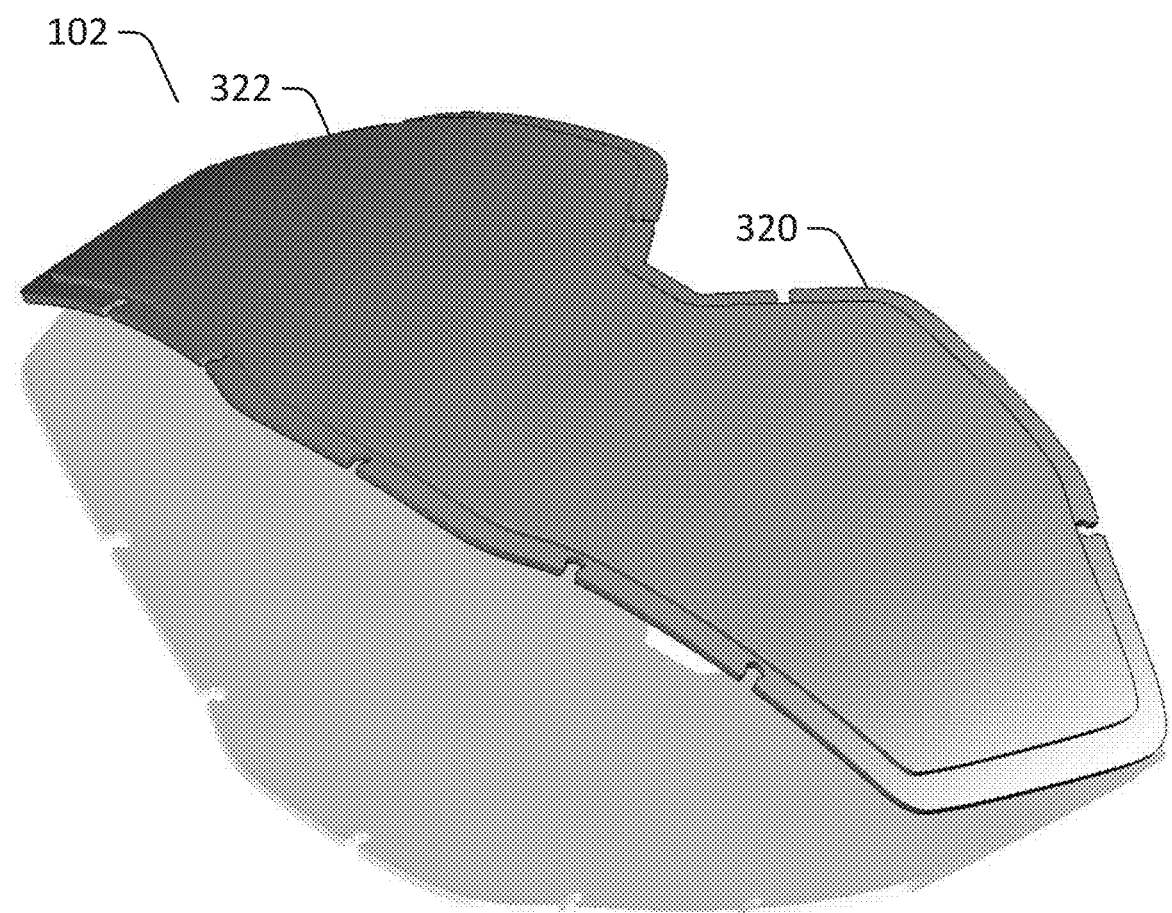
FIGS. 4A-C illustrate isometric views of a multi-thickness lens, in accordance with an example of the disclosure.
Figure 4B:
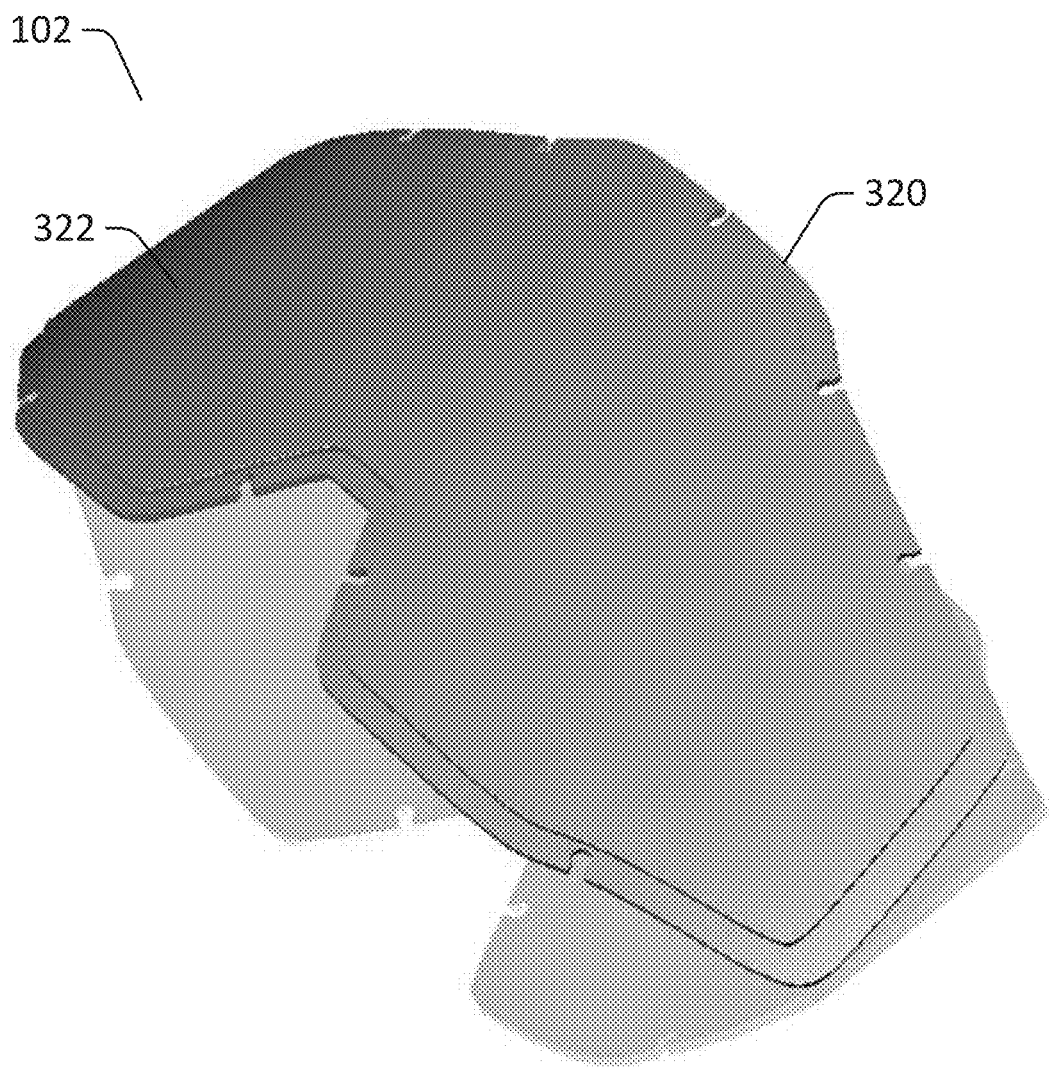
Figure 4C:
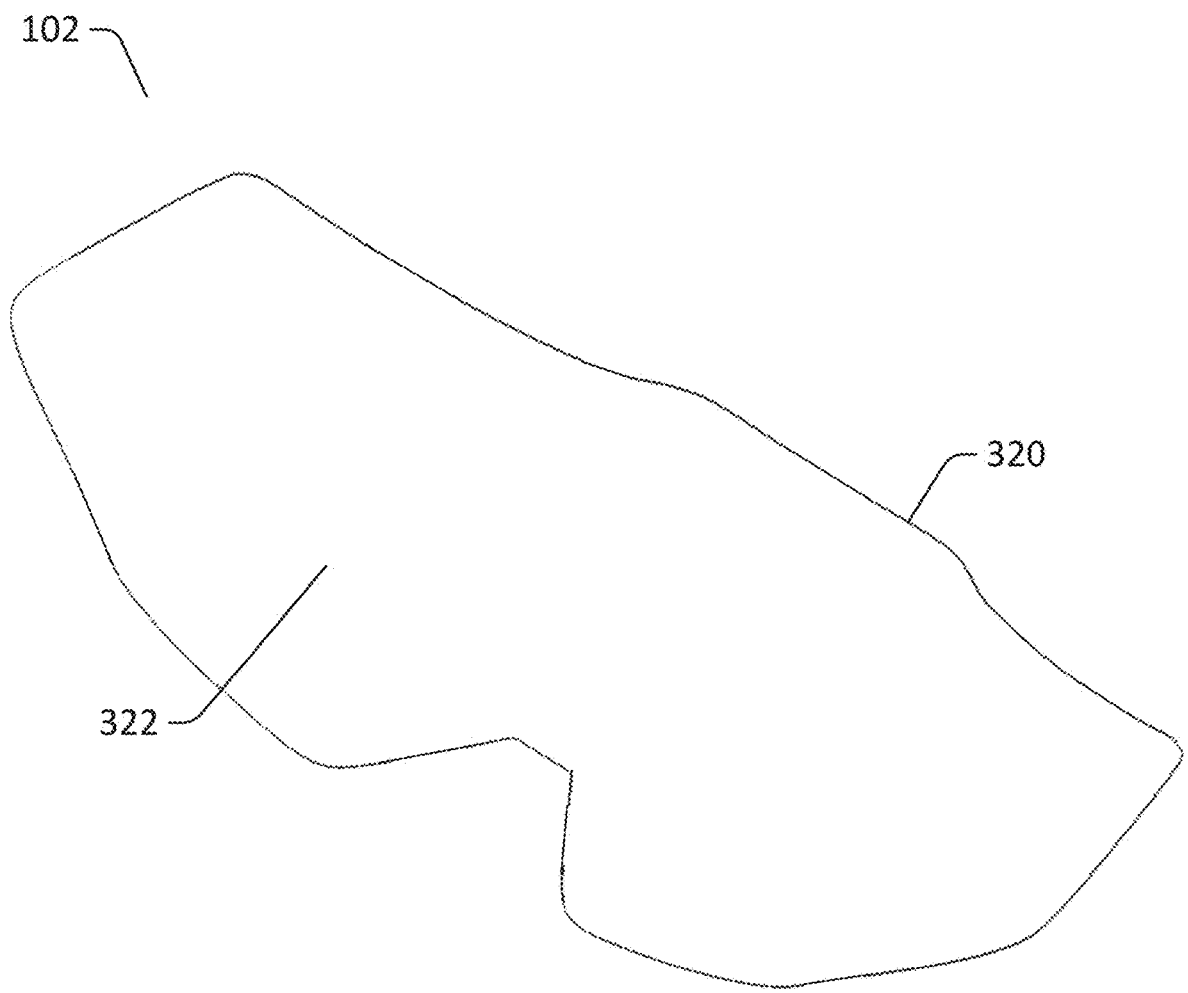

As shown in FIG. 3C, in certain embodiments, the front of the lens 102 may include a goggle lens viewing portion 322 that is raised with respect to the goggle lens perimeter portion 320 while the goggle lens viewing portion 322 may be level with that of the goggle lens perimeter portion 320 on the rear of the lens 102, or vice versa. Other embodiments may include raised goggle lens perimeter portions 320 on both the front and bottom of the lens 102.

As shown in FIG. 4C, in certain embodiments, the goggle lens viewing portion 322 may be level with the goggle lens perimeter portion 320 on at least one side of the goggle lens 102. FIG. 4C may, for example, show a back side (e.g., the side closer to a user's eyes) of the goggle lens 102. In certain embodiments of the goggle lens 102, the front side of the goggle lens 102 may include a goggle lens viewing portion 322 that is not level with the goggle lens perimeter portion 320.

FIG. 4C may also illustrate an embodiment of the goggle lens 102 that may not include attachment features. In such an embodiment, the attachment features 324A-I, for example, may not be present and/or may be replaced with other attachment features such as other types of slots, holes, hooks, snaps, cutouts, and/or other such features. In certain such embodiments, the goggle lens 102 may not have any attachment features and may, instead, be configured to be held in place within the goggle 100 by being inserted into grooves and/or other features.

Figure 5:
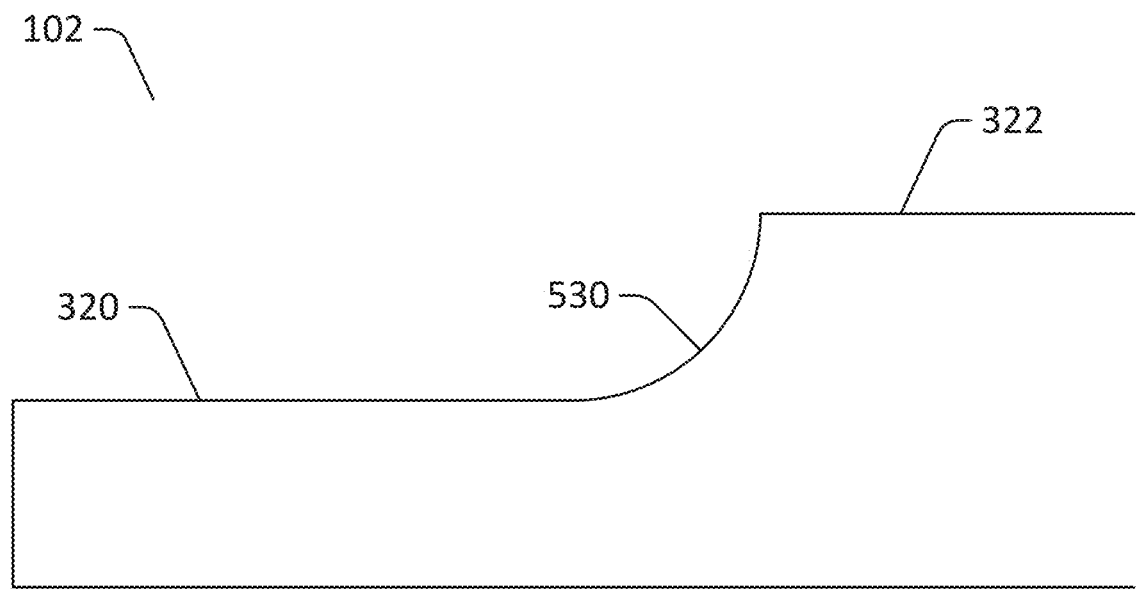
FIGS. 5-7 illustrate simplified representations of details of a sports goggle with a multi-thickness lens, in accordance with an example of the disclosure.
Figure 6:
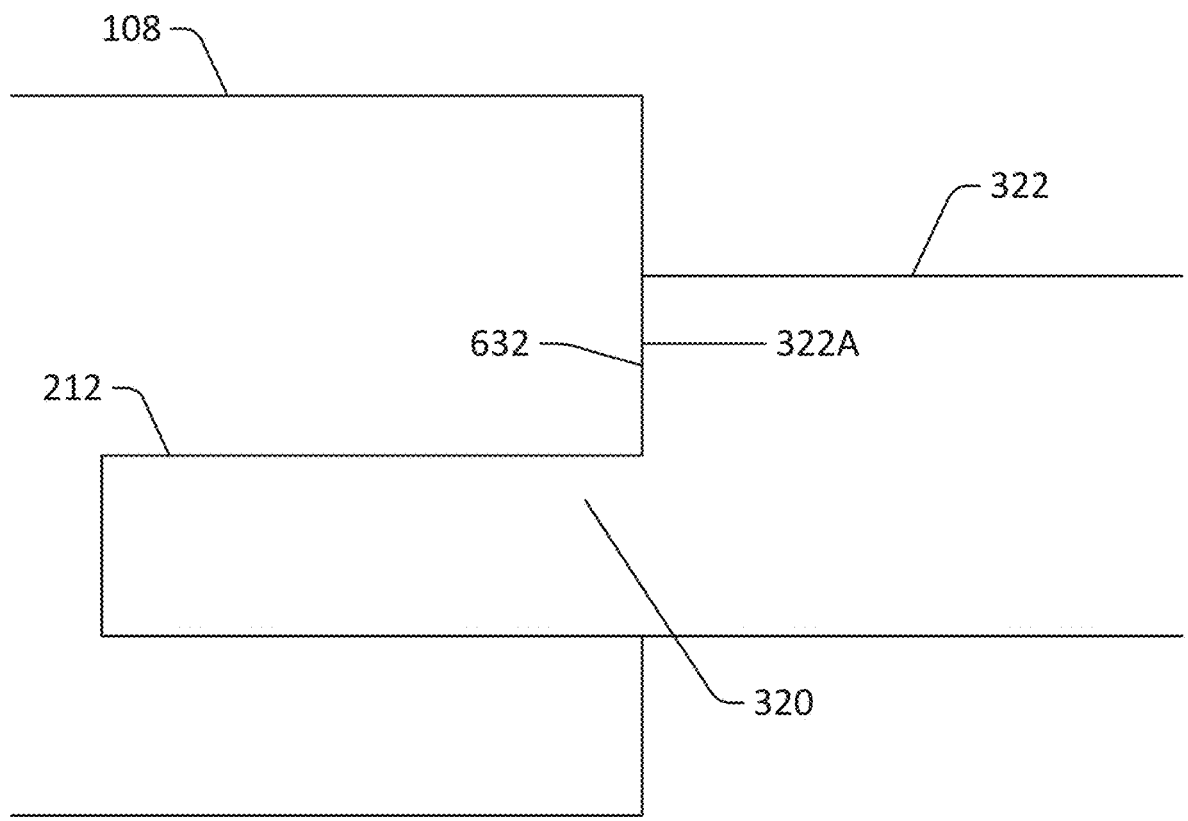
Figure 7:
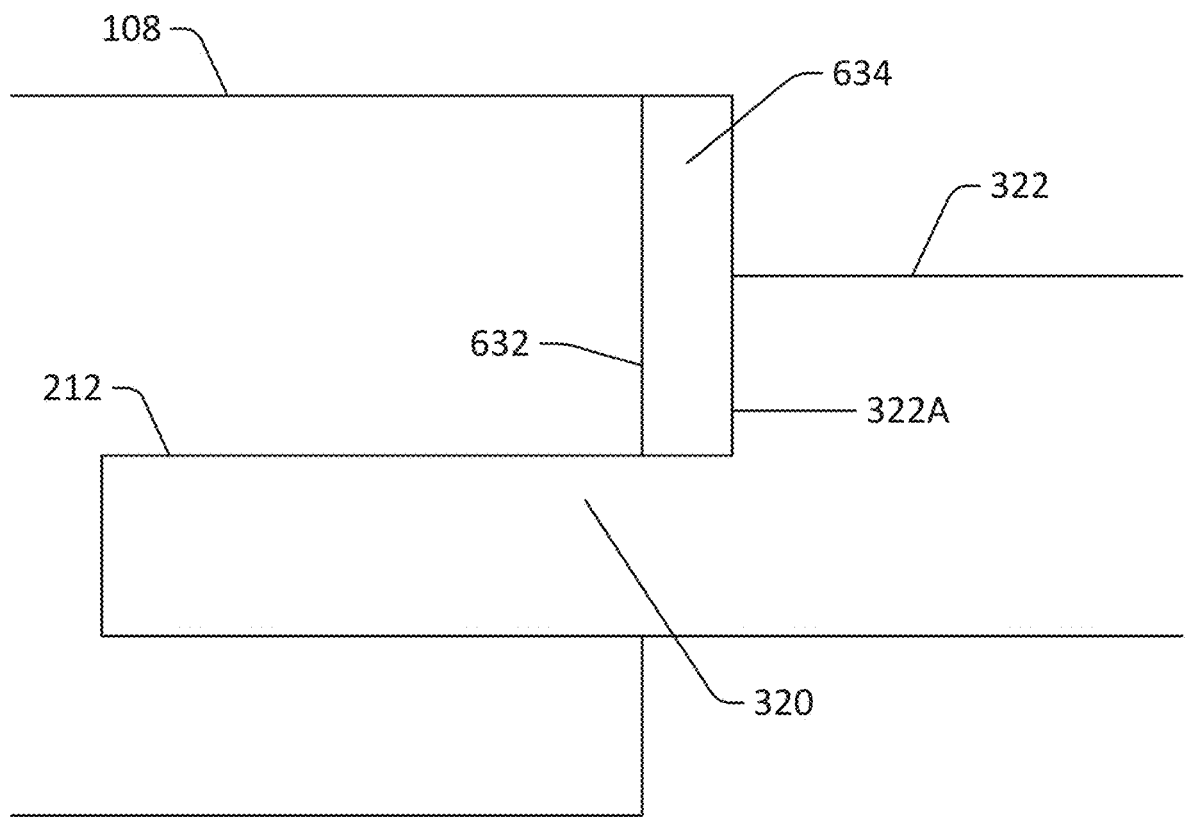

FIGS. 5-7 illustrate simplified representations of details of a sports goggle with a multi-thickness lens, in accordance with an example of the disclosure. FIG. 5 illustrates a simplified representation of the lens 102 where the transition between the goggle lens viewing portion 322 and the goggle lens perimeter portion 320 is at least partially smooth. In FIG. 5, the transition between the goggle lens viewing portion 322 and the goggle lens perimeter portion 320 may include a radius 530. In certain other embodiments, the transition may be smoothed by, for example, a chamfer, curves of a plurality of radii, and/or other techniques of forming a gradual transition between the goggle lens viewing portion 322 and the goggle lens perimeter portion 320.

FIG. 6 illustrates a simplified representation of a lens 102 that is configured to transfer stresses to a goggle 100. In FIG. 6, the groove 212 may be disposed within the second goggle frame portion 108. Other embodiments may dispose the groove 212 within the first goggle frame portion 106 and/or may be formed by a combination of the second goggle frame portion 108, the first goggle frame portion 106, or through one or more other components of the goggle 100 alternatively or in combination.

In FIG. 6, the second goggle frame portion 108 may include a surface 632 that may be configured to rest against at least a portion of a surface 322A of the goggle lens viewing portion 322. In certain embodiments, the surface 322A of the goggle lens viewing portion 322 or a portion thereof may contact the surface 632 and/or be in contact such that the goggle lens viewing portion 322 is "preloaded" against the surface 632. In such embodiments, forces and/or stresses experienced by the goggle lens viewing portion 322 may be transferred from the goggle lens viewing portion 322 to the second goggle frame portion 108 via the surface 322A. Additionally, "pre-loading" the goggle lens viewing portion 322 and/or the lens 102 may increase the rigidity of the goggle lens viewing portion 322 and further reduce the possibility of damage from impacts.

FIG. 7 illustrates an additional simplified representation of a lens 102 that is configured to transfer stresses to a goggle 100. In FIG. 7, the groove 212 may also be disposed within the second goggle frame portion 108. Additionally, in FIG. 7, an adapter 634 may be disposed between the surface 322A of the lens 102 and the surface 632 of the second goggle frame portion 108. The adapter 634 may be, for example, a component that may allow a multi-thickness lens 102 to be adapted to fit within the goggle 100 (e.g., a component that may allow a multi-thickness lens 102 to couple to certain attachment features), a gasket that may allow the lens 102 to transfer force from the lens 102 to the first goggle frame portion 106 and/or the second goggle frame portion 108, and/or another component that may allow the lens 102 to be received by the goggle 100.

In certain embodiments, the adapter 634 may allow the lens 102 to expand and/or deform for a first distance. For example, the adapter 634 may deform or occupy space left by certain multi-thickness lens 102 to improve the look, function, and/or ease of assembling of the lens 102 to the goggle 100 (e.g., the first goggle frame portion 106 and/or the second goggle frame portion 108). The adapter 634 may additionally aid in the transfer of forces and/or stresses from the lens 102 to the second goggle frame portion 108. As such, the adapter 634 may allow for transfer of forces and/or stresses or a portion thereof while still minimizing stresses experienced by the lens 102 through deflection and/or expansion.

In certain embodiments, an adapter may be disposed within the goggle 100 when a multi-thickness lens is coupled to the goggle 100. Such an adapter may be, for example, the adapter 634, a component with attachment features configured to couple to the lens 102 and/or other portions of the goggle 100, and/or other components that may allow for the multi-thickness lens 102 to be fitted within a goggle 100 that may be configured to receive a standard lens.

Figure 8:
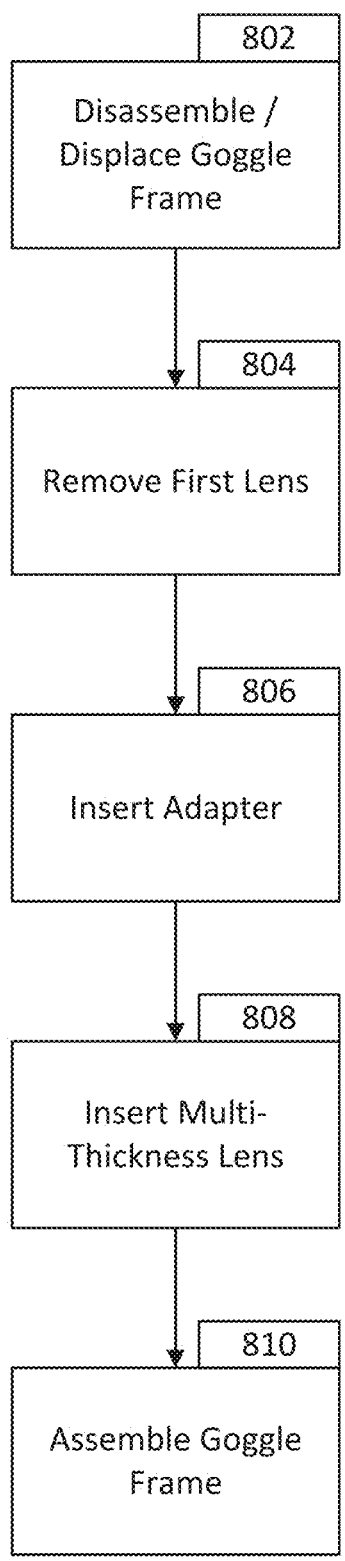
FIG. 8 shows a flowchart illustrating an assembly process of a sports goggle with a multi-thickness lens, in accordance with an example of the disclosure.

FIG. 8 shows a flowchart illustrating an assembly process of a sports goggle with a multi-thickness lens, in accordance with an example of the disclosure. In block 802, the goggle frame or portions of the goggle frame may be disassembled and/or displaced. After the goggle frame is disassembled and/or displaced, a first lens disposed within the goggle may be removed in block 804.

After the first lens has been removed, in optional block 806, an adapter may be inserted and/or fitted to the goggle. The adapter may be configured to receive a multi-thickness lens for the goggle and/or may be configured to help distribute stresses from the lens. In block 808, a multi-thickness lens such as the lens 102 may be inserted and/or fitted to the goggle. After the multi-thickness lens has been inserted and/or fitted, the goggle frame and/or portions of the goggle frame may be assembled.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected is:

1. A goggle comprising:
a goggle frame having a groove; and
a lens coupled to the goggle frame, the lens comprising a body and a peripheral flange extending around the body, wherein a rear surface of the body is configured to be disposed closer to a face of a user than an opposing front surface of the body when the goggle is in use;
wherein the body of the lens has a same minimum first thickness throughout the body and the peripheral flange is stepped down from the front surface to a second thickness smaller than the first thickness;
wherein the rear surface of the body and the rear surface of the peripheral flange collectively form a single curved expanse, and the peripheral flange is sandwiched in the groove by the goggle frame; and
wherein the peripheral flange and the body of the lens are formed integrally from a single material.

2. The goggle of claim 1, wherein the second thickness is approximately 0.8 millimeters.

3. The goggle of claim 1, wherein the peripheral flange comprises one or more attachment features configured to couple to the goggle frame.

4. The goggle of claim 3, wherein:
the one or more attachment features comprise a plurality of slots formed in the peripheral flange.

5. The goggle of claim 1, wherein the second thickness is between 0.2 millimeters and 1.6 millimeters.

6. A method of making the goggle of claim 1, comprising:
forming the goggle frame; and
forming the peripheral flange and the body of the lens as a single piece.

7. A method of assembling the goggle of claim 1, the method comprising:
removing a first goggle lens from the goggle frame;
inserting the peripheral flange into the groove of the goggle frame; and
disposing the body of the lens such that a side surface of the body of the lens abuts a first surface of the goggle frame, the first surface of the goggle frame being adjacent the groove.

8. The method of claim 7, further comprising:
disposing an adapter between the goggle frame and the side surface of the body of the lens.

9. A goggle comprising:
a goggle frame having a groove; and
a lens coupled to the goggle frame, the lens comprising a body and a peripheral flange extending around the body, wherein the lens has a rear surface configured to be disposed closer to a face of a user than an opposing front surface of the lens when the goggle is in use;
wherein the body of the lens has a first thickness and the peripheral flange has a second thickness smaller than the first thickness, the rear surface of the body and the rear surface of the peripheral flange collectively form a single curved expanse, and the peripheral flange is sandwiched in the groove by the goggle frame; and
wherein the lens further comprises a goggle lens transition portion disposed between the peripheral flange and the body of the lens, wherein the goggle lens transition portion is the first thickness at a first end disposed next to the body of the lens and is the second thickness at a second end disposed next to the peripheral flange.

10. The goggle of claim 9, wherein the goggle lens transition portion is continuous from the body of the lens to the peripheral flange.

11. The goggle of claim 9, wherein the body of the lens is dimensioned such that a side surface of the body of the lens engages the goggle frame to preload the body of the lens against the goggle frame and transfer one or more stresses experienced by the body of the lens to the goggle frame.

12. The goggle of claim 11, further comprising an adapter configured to be disposed between the goggle frame and the side surface of the body of the lens and to couple the lens to the goggle frame.

13. The goggle of claim 11, wherein the side surface of the body of the lens forms a stepped transition between the body of the lens and the peripheral flange.

14. The goggle of claim 9, wherein the peripheral flange and the body of the lens are formed integrally from a single material.

15. The goggle of claim 9, wherein the peripheral flange comprises one or more attachment features configured to couple to the goggle frame.

16. The goggle of claim 9, wherein the goggle frame includes a flexible portion configured to couple to the peripheral flange, and the lens is flexible.

* * * * *